(12) United States Patent
Yamashita et al.

(10) Patent No.: US 10,898,135 B2
(45) Date of Patent: Jan. 26, 2021

(54) BIOMETRIC INFORMATION MEASUREMENT DEVICE, BIOMETRIC INFORMATION MANAGEMENT METHOD, AND BIOMETRIC INFORMATION MANAGEMENT PROGRAM

(71) Applicants: OMRON HEALTHCARE CO., LTD., Kyoto (JP); OMRON CORPORATION, Kyoto (JP)

(72) Inventors: Shingo Yamashita, Muko (JP); Naoki Maeda, Kyoto (JP)

(73) Assignees: OMRON HEALTHCARE CO., LTD., Kyoto (JP); OMRON CORPORATION, Kyoto (JP)

(*) Notice: Subject to any disclaimer, the term of this patent is extended or adjusted under 35 U.S.C. 154(b) by 0 days.

(21) Appl. No.: 16/444,289

(22) Filed: Jun. 18, 2019

(65) Prior Publication Data

US 2019/0298260 A1 Oct. 3, 2019

Related U.S. Application Data

(63) Continuation of application No. PCT/JP2017/038808, filed on Oct. 26, 2017.

(30) Foreign Application Priority Data

Dec. 19, 2016 (JP) .................................. 2016-245696

(51) Int. Cl.
*G06F 21/00* (2013.01)
*A61B 5/00* (2006.01)
(Continued)

(52) U.S. Cl.
CPC ................ *A61B 5/681* (2013.01); *A61B 5/02* (2013.01); *A61B 5/0265* (2013.01);
(Continued)

(58) Field of Classification Search
CPC ............... A61B 5/681; A61B 5/02405; A61B 5/02438; A61B 5/6824; A61B 5/6831;
(Continued)

(56) References Cited

U.S. PATENT DOCUMENTS 9,614,829 B1 * 4/2017 Molina-Markham ........................ H04L 63/08
9,942,222 B1 * 4/2018 Fenton ................ H04L 63/0853
(Continued)

FOREIGN PATENT DOCUMENTS

| JP | 11-282754 | 10/1999 |
|----|-----------|---------|
| JP | 2002-238877 | 8/2002 |

(Continued)

OTHER PUBLICATIONS

International Search Report dated Dec. 19, 2017 in International (PCT) Application No. PCT/JP2017/038808 w/English translation.

*Primary Examiner* — Brandon S Hoffman
*Assistant Examiner* — William A Corum, Jr.
(74) *Attorney, Agent, or Firm* — Wenderoth, Lind & Ponack, L.L.P.

(57) ABSTRACT

A biometric information measurement device intermittently measures biometric information from a living body. The device includes an attachment and detachment determining section which determines whether the device is in an attached state where the device is attached to the living body or an unattached state where the device is detached from the living body, a personal identifying section which, in the attached state, determines whether a user attached with the device is a registered user who is registered in advance and stores a result of the determination, and a storage controller which, when a determination result indicating that the user is the registered user is stored, stores information indicating the registered user while being associated with the measured biometric information. The personal identifying section
(Continued)

deletes the determination result when a time period in which the device is determined to be in the unattached state exceeds a predetermined time period.

4 Claims, 5 Drawing Sheets

(51) Int. Cl.
| | |
|---|---|
| *G16H 10/60* | (2018.01) |
| *A61B 5/024* | (2006.01) |
| *G06F 21/32* | (2013.01) |
| *A61B 5/02* | (2006.01) |
| *A61B 5/0265* | (2006.01) |
| *G16H 40/63* | (2018.01) |
| *A61B 5/0205* | (2006.01) |
| *A61B 5/021* | (2006.01) |

(52) U.S. Cl.
CPC ...... *A61B 5/02405* (2013.01); *A61B 5/02438* (2013.01); *A61B 5/6824* (2013.01); *A61B 5/6831* (2013.01); *G06F 21/32* (2013.01); *G16H 10/60* (2018.01); *A61B 5/02055* (2013.01); *A61B 5/02108* (2013.01); *G16H 40/63* (2018.01)

(58) Field of Classification Search
CPC . A61B 5/02055; A61B 5/02108; G06F 21/32; G16H 10/60; G16H 40/63
See application file for complete search history.

(56) References Cited

U.S. PATENT DOCUMENTS

| | | |
|---|---|---|
| 2002/0013717 A1 | 1/2002 | Ando et al. |
| 2008/0216171 A1* | 9/2008 | Sano .......................... H04L 9/32 726/19 |
| 2015/0135310 A1* | 5/2015 | Lee ........................ A61B 5/681 726/20 |
| 2016/0154952 A1* | 6/2016 | Venkatraman ...... H04L 63/0861 705/44 |
| 2016/0354033 A1 | 12/2016 | Ouchi et al. |

FOREIGN PATENT DOCUMENTS

| | | |
|---|---|---|
| JP | 2013-212315 | 10/2013 |
| JP | 2015-150375 | 8/2015 |

\* cited by examiner

BIOMETRIC INFORMATION MEASUREMENT DEVICE, BIOMETRIC INFORMATION MANAGEMENT METHOD, AND BIOMETRIC INFORMATION MANAGEMENT PROGRAM

CROSS-REFERENCE TO RELATED APPLICATIONS

This is a Continuation of International Patent Application No. PCT/JP2017/038808 filed Oct. 26, 2017, which claims the benefit of Japanese Patent Application No. 2016-245696 filed Dec. 19, 2016. The disclosures of the prior applications are hereby incorporated by reference herein in their entireties.

TECHNICAL FIELD

The present invention relates to a biometric information measurement device, a biometric information management method, and a biometric information management program.

BACKGROUND ART

There has been generally known, as a personal authentication technique for enabling only a specific individual to use a device, a service, or the like, techniques using information specific to a living body, such as fingerprint authentication, facial image authentication, iris authentication, or vein authentication.

Patent Literature 1 (JP-A-2013-212315) discloses a vital sensor which performs an authentication process using a vein pattern when the sensor is attached to a wrist. If the user is a registered user, the vital sensor stores measured biometric information while associating the biometric information with authentication information indicating the registered user, whereas if the user is an unregistered user, the vital sensor stores the measured biometric information while associating the biometric information with authentication information indicating an unregistered user. When the sensor is detached from the wrist, respective functions are disabled.

Patent Literature 2 (JP-A-2002-238877) discloses an exercise monitor which performs determination on whether the monitor is attached to a living body and determination on whether a user wearing the monitor is a registered user (determination by fingerprint authentication or the like). When these determination are completed, the exercise monitor encrypts exercise information that are measured by the monitor and displays the information.

Patent Literature 3 (JP-A-2015-150375) discloses a system including a wearable type biometric information measurement device, and a biometric information collection device which is attached to the arm of a human and collects measurement results of biometric information measured by the biometric information measurement device. When the biometric information collection device is attached to the user, the biometric information collection device starts an authentication process. Authentication information used in authentication is validated while the biometric information collection device is attached to the user, whereas the authentication information is invalidated when the attachment is released, so as to achieve high level security.

Various devices require personal authentication. An example of such a device is a biometric information measurement device which intermittently measures biometric information such as blood pressure information (systolic blood pressure, diastolic blood pressure, pulse pressure, or the like), pulsation information (pulse rate or the like), heartbeat information (heart rate or the like), or vascular property information. Such a biometric information measurement device is used for diagnosis or the like by being attached to a living body for a long time period such as half a day or one day. The vascular property information includes AI (Augmentation Index), PTT (Pulse Transit Time), or the like.

In order to appropriately perform diagnosis, biometric information which is measured and stored by a biometric information measurement device should include data that are measured from a person who is a diagnosis target.

According to the vital sensor disclosed in Patent Literature 1, the biometric information which is measured from a registered user and the biometric information which is measured from an unregistered user can be stored while being clearly distinguished from each other. Therefore, appropriate diagnosis can be performed using data that are measured from the person who is a diagnosis target.

However, when the vital sensor is detached from the wrist, respective functions are disabled. In the case where, for example, the vital sensor is loosely attached to the wrist such that the sensor can move with respect to the wrist, it is possibly erroneously determined that the vital sensor is detached from the wrist due to some motion of the wrist. In such a case, the measurement of biometric information is stopped, and also a result of personal authentication is invalidated, so that the usability is poor.

In Patent Literature 2, an operation in the case where the monitor is detached from the living body is not considered.

In the device disclosed in Patent Literature 3, when the device is detached from the living body, authentication information is invalidated. In the case where it is erroneously determined that the device is detached from the living body, a result of personal authentication is invalidated, so that the usability is poor.

SUMMARY

Embodiments of the present invention address the above disadvantages and other disadvantages not described above. However, the present invention is not required to overcome the disadvantages described above, and thus, an exemplary embodiment of the present invention may not overcome any of the problems described above.

A biometric information measurement device according to an embodiment of the present invention intermittently measures biometric information from a living body in a state of being attached to the living body. The biometric information measurement device includes: an attachment and detachment determining section which determines whether the device is in an attached state where the biometric information measurement device is attached to the living body or in a unattached state where the biometric information measurement device is detached from the living body; a personal identifying section which, in the attached state, determines whether a user attached with the biometric information measurement device is a registered user who is registered in advance and stores a result of the determination; and a storage controller which, when a determination result indicating that the user is the registered user is stored, stores information indicating the registered user while being associated with the measured biometric information. The personal identifying section deletes the determination result when a time period in which the device is determined to be in the unattached state exceeds a predetermined time period.

A biometric information management method according to an embodiment of the present invention manages biometric information that is measured by a biometric information measurement device which intermittently measures biometric information from a living body in a state where the device is attached to the living body. The method includes: determining whether the device is in an attached state where the biometric information measurement device is attached to the living body or an unattached state where the biometric information measurement device is detached from the living body; in the attached state, determining whether a user attached with the biometric information measurement device is a registered user who is registered in advance and storing a result of the determination; when a determination result indicating that the user is the registered user is stored, storing information indicating the registered user while being associated with the measured biometric information; and when a time period in which the device is determined to be in the unattached state exceeds a predetermined time period, deleting the determination result.

A biometric information management program according to an embodiment of the present invention is a program for managing biometric information that is measured by a biometric information measurement device which intermittently measures biometric information from a living body in a state where the device is attached to the living body. The program causes a computer to: determine whether the device is in an attached state where the biometric information measurement device is attached to the living body or in an unattached state where the biometric information measurement device is detached from the living body; in the attached state, determine whether a user attached with the biometric information measurement device is a registered user who is registered in advance and store a result of the determination; when a determination result indicating that the user is the registered user is stored, store information indicating the registered user while being associated with the measured biometric information; and when a time period in which the device is determined to be in the unattached state exceeds a predetermined time period, delete the determination result.

BRIEF DESCRIPTION OF DRAWINGS

The above and other aspects of the present invention will become more apparent and more readily appreciated from the following description of embodiments of the present invention taken in conjunction with the attached drawings.

DESCRIPTION OF EMBODIMENTS

Hereinafter, an embodiment of the present invention will be described with reference to the drawings.

Figure 1:
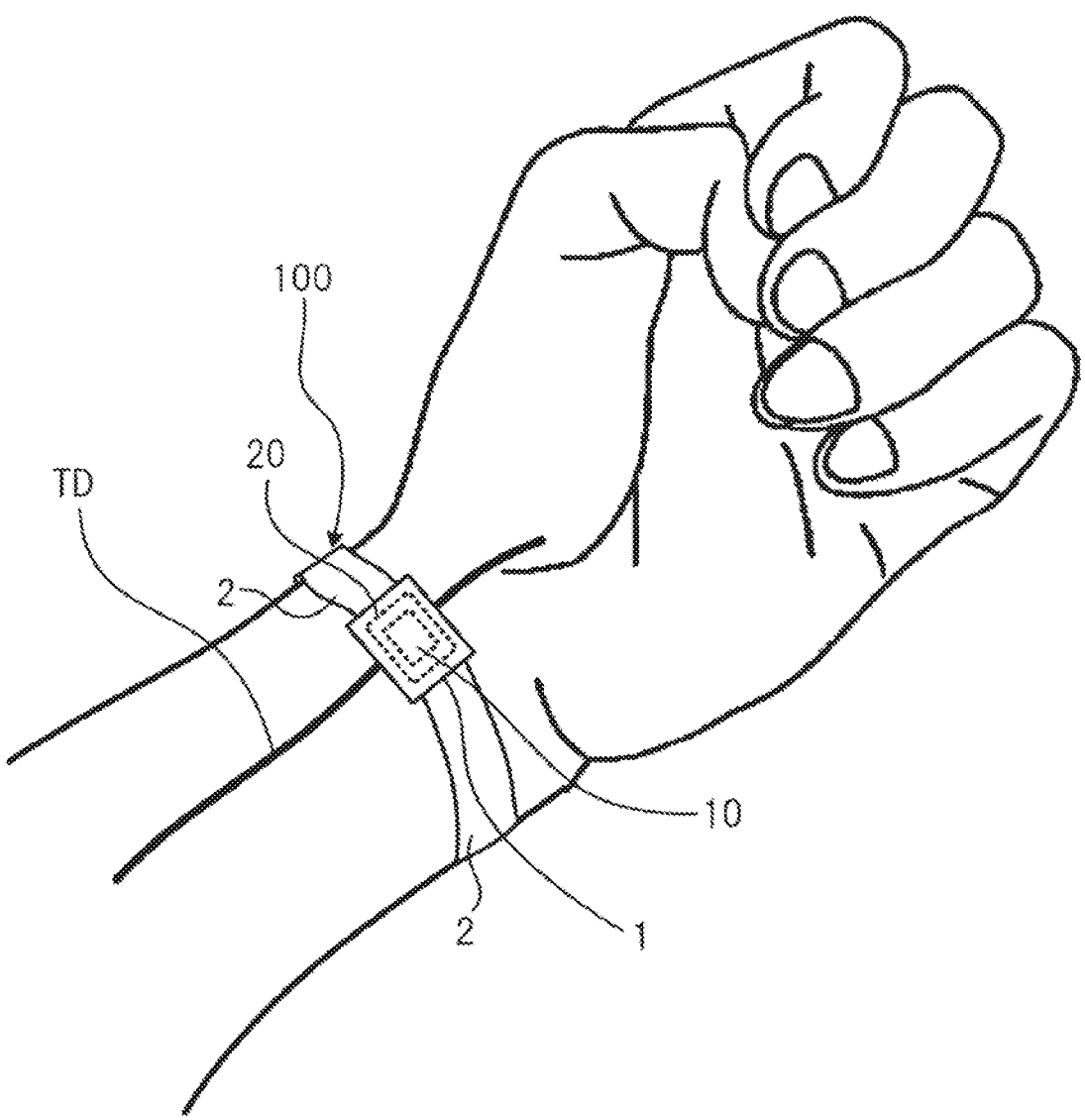
FIG. 1 is a schematic diagram showing the configuration of the appearance of a biometric information measurement device 100 for illustrating an embodiment of the present invention.

FIG. 1 is a schematic diagram showing the configuration of the appearance of a biometric information measurement device 100 for illustrating an embodiment of the present invention.

The biometric information measurement device 100 includes a main unit 1, and a belt 2 fixed to the main unit 1. The biometric information measurement device 100 is used while being attached to a wrist in which a radial artery TD that is a measurement target of biometric information is present under a skin, and specifically, used while the main unit 1 is attached to the wrist by the belt 2. Biometric information which is the measurement target by the biometric information measurement device 100 is blood pressure information, pulsation information, heartbeat information, vascular property information, or the like.

The main unit 1 of the biometric information measurement device 100 includes a pressure sensor 10 which detects a pressure pulse wave from the radial artery TD, and a pressing mechanism 20 which presses the pressure sensor 10 against the wrist.

Figure 2:
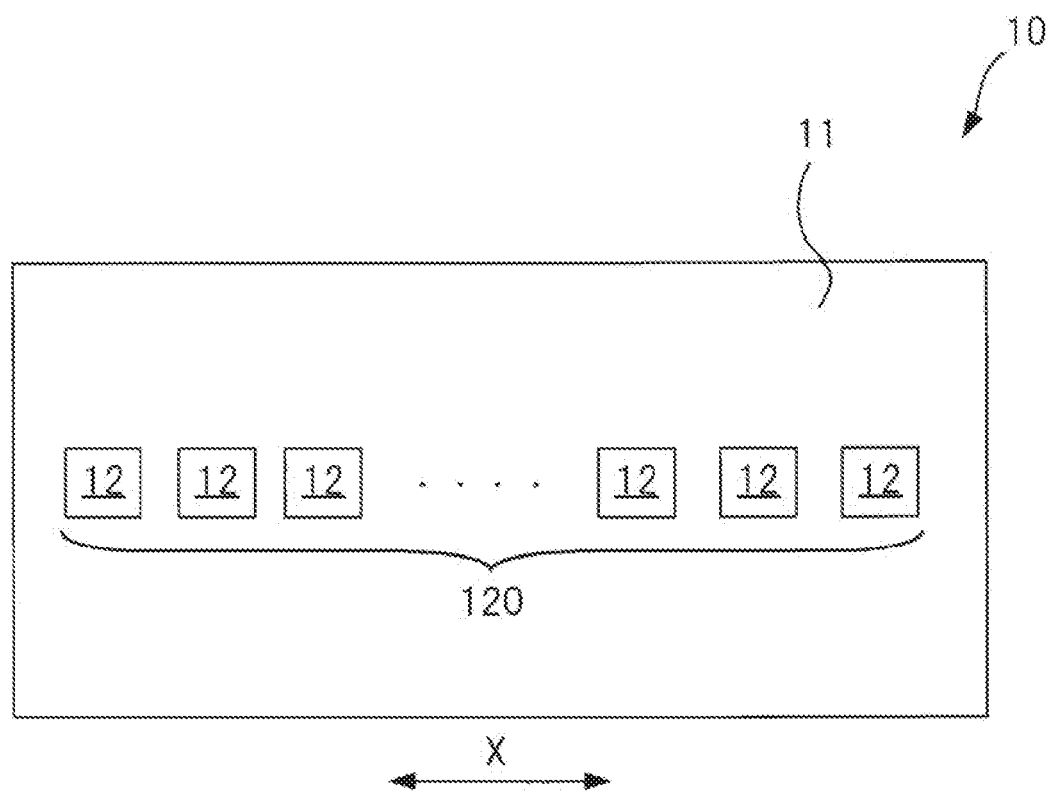
FIG. 2 is a schematic plan diagram of a pressure sensor 10 of the biometric information measurement device 100 shown in FIG. 1, as viewed from the side of a contact plane with a wrist.

FIG. 2 is a schematic plan diagram of the pressure sensor 10 of the biometric information measurement device 100 shown in FIG. 1, as viewed from the side of a contact plane with the wrist. As shown in FIG. 2, the pressure sensor 10 includes an element row 120 which is formed on a planar substrate 11.

The element row 120 includes a plurality of pressure detecting elements 12 which are arranged in a direction X that is one direction. As the pressure detecting elements 12, any kind of elements which detect a pressure and convert the pressure into an electric signal may be used, and for example, elements utilizing the piezoresistance effect may be used.

The intervals of the plurality of pressure detecting elements 12 in the arrangement direction are sufficiently small such that a necessary and sufficient number of elements can be arranged above the radial artery TD. The distance between the pressure detecting elements which are at the both ends of the plurality of pressure detecting elements 12 is necessarily and sufficiently larger than the diameter of the radial artery TD.

The pressure sensor 10 is pressed against the wrist by the pressing mechanism 20 in a state where the direction X that is the arrangement direction of the plurality of pressure detecting elements 12 included in the element row 120 intersects with the extension direction of the radial artery TD. Alternatively, the pressure sensor 10 may have a configuration where a plurality of element rows 120 are arranged on the substrate 11 in a direction perpendicular to the direction X.

Figure 3:
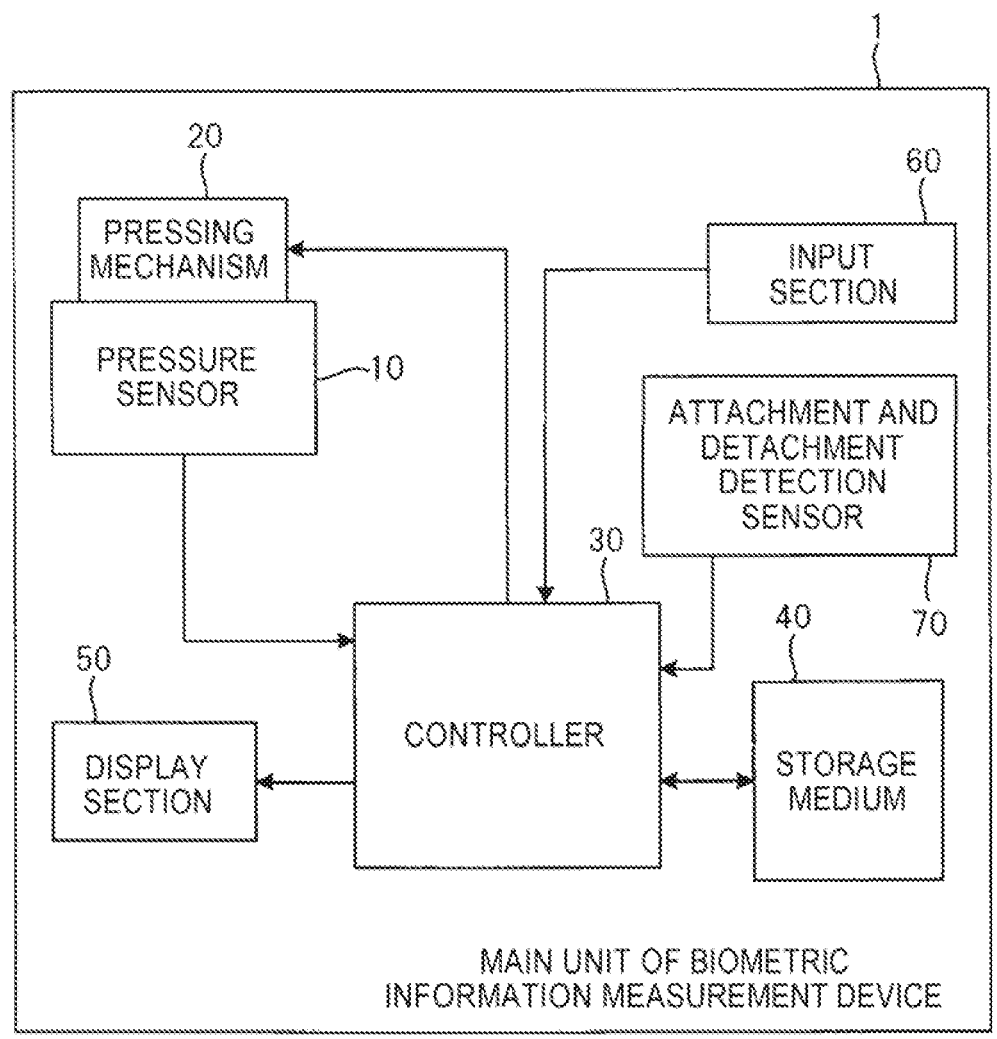
FIG. 3 is a diagram showing the internal hardware configuration of a main unit 1 of the biometric information measurement device 100 shown in FIG. 1.

FIG. 3 is a diagram showing the internal hardware configuration of the main unit 1 of the biometric information measurement device 100 shown in FIG. 1.

The main unit 1 includes the pressure sensor 10, the pressing mechanism 20, a controller 30 which generally performs entire control, a storage medium 40, a display section 50, an input section 60, and an attachment and detachment detection sensor 70.

The pressing mechanism 20 includes, for example, an air bag that is fixed to the surface of the substrate 11 opposite to the surface on which the element row 120 is formed, and a pump for adjusting the internal pressure of the air bag. The pressing force (the internal pressure of the pump) which is applied to the wrist by the pressing mechanism 20 is controlled by the controller 30. The pressing mechanism 20 may be configured by any kind of device as far as it can press the pressure sensor 10 against the wrist and is not limited to a configuration in which an air bag is used.

The pressure sensor 10 supplies pressure signals which are detected by the pressure detecting elements 12 constituting the element row 120, to the controller 30.

The controller 30 includes a ROM (Read Only Memory), a RAM (Random Access Memory), and a processor, and generally controls the entire main unit 1 by executing programs stored in the ROM by the processor. The RAM functions as a work memory when the controller 30 performs various processes.

The storage medium 40 is a medium in and from which data can be stored and read, and for example, a flash memory may be used as the medium. The storage medium 40 may be of the mobile type such as a memory card, or fixed to the main unit 1 to be undetachable.

The display section 50 displays various kinds of information containing biometric information and includes a liquid crystal display device or the like.

The input section 60 is a device for inputting information (hereinafter, referred to as identification information) necessary to identify a person. The identification information is information inherent to the living body, such as fingerprint information, voiceprint information, facial image information, iris information, or vein information.

The attachment and detachment detection sensor 70 determines whether the biometric information measurement device 100 is in an attached state where the biometric information measurement device 100 is attached to the living body or in an unattached state where the biometric information measurement device 100 is detached from the living body.

As the attachment and detachment detection sensor 70, there is used a sensor for detecting a contact with an object, such as a capacitance touch sensor or a pressure sensor, or a sensor for detecting a contact with a living body based on a shape change of the main unit 1 of the biometric information measurement device 100, such as an expansion sensor or a bend sensor.

Figure 4:
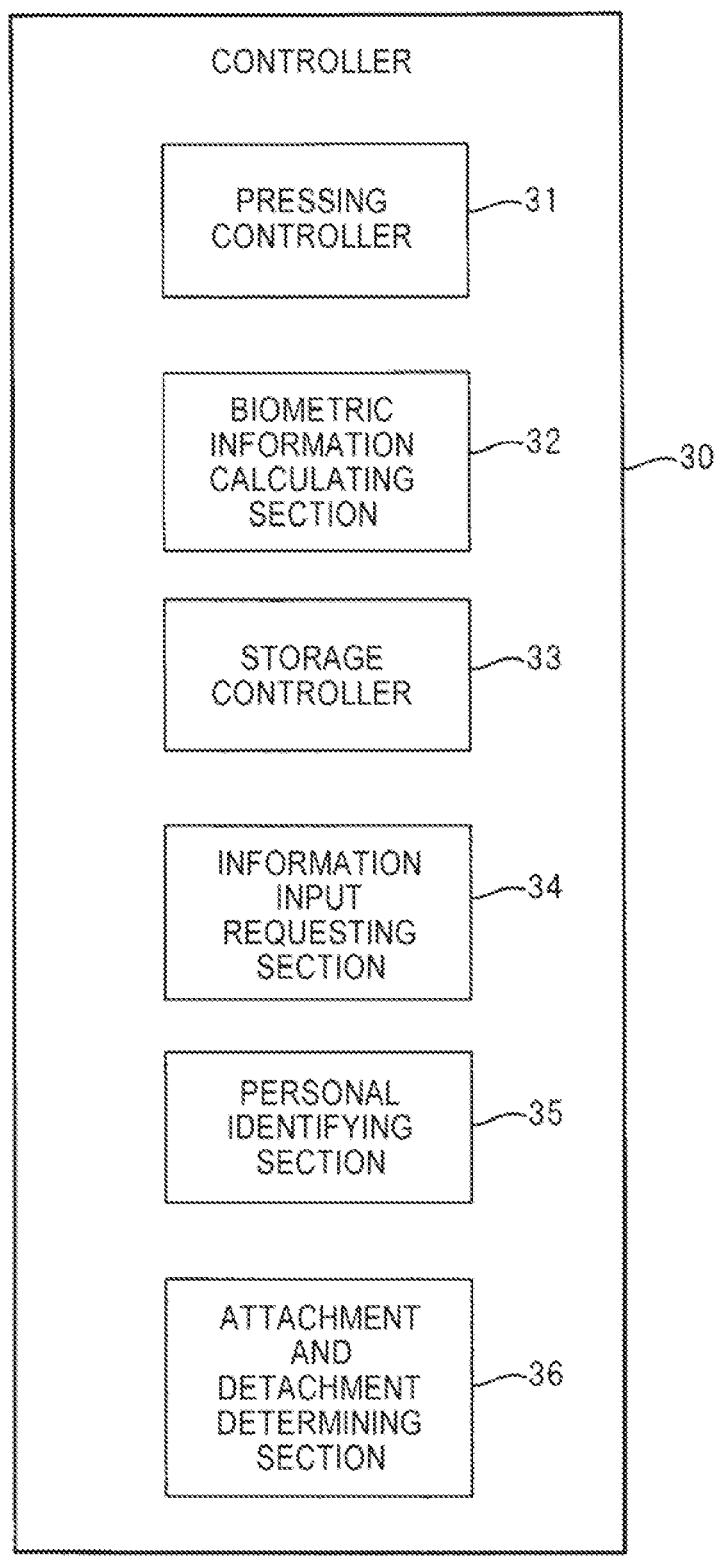
FIG. 4 is a functional block diagram of a controller 30 shown in FIG. 3.

FIG. 4 is a functional block diagram of the controller 30 shown in FIG. 3.

The controller 30 executes programs stored in the ROM which is a non-transitory computer readable medium, to function as a pressing controller 31, a biometric information calculating section 32, a storage controller 33, an information input requesting section 34, a personal identifying section 35, and an attachment and detachment determining section 36. The programs include a biometric information management program.

The pressing controller 31 drives the pressing mechanism 20 to control the pressing force of the pressure sensor 10 against the wrist applied by the pressing mechanism 20.

The biometric information calculating section 32 calculates, every one or plural pulse, biometric information such as blood pressure information, pulsation information, heartbeat information, or vascular property information based on information of the pressure pulse wave which is detected by the optimum pressure detecting element of the plurality of pressure detecting elements 12 constituting the element row 120, in a state where the pressure sensor 10 is pressed against the wrist with the optimum pressing force by the pressing mechanism 20. In this specification, description will be made with the assumption that the calculation of biometric information and the measurement of biometric information are synonymous with each other.

The optimum pressing force is a pressing force which realizes a state where a pressure pulse wave can be detected from the radial artery TD that is pressed with the optimum pressing force, without being affected by the tension in the circumferential direction of the blood vessel, i.e., the tonometry state. The optimum pressure detecting element is the pressure detecting element 12 which is located directly above a portion of the radial artery TD that is pressed and flattened with the optimum pressing force by the pressure sensor 10.

The information input requesting section 34 requests an input of identification information through the input section 60 in the state where the biometric information measurement device 100 is attached to the living body. Although the timing when the information input requesting section 34 requests an input of identification information is arbitrarily set, the timing may set to, for example, a timing before the start of the measurement of the biometric information.

The personal identifying section 35 determines whether the user attached with the biometric information measurement device 100 is a registered user who is registered in advance based on the identification information which is input in response to the request by the information input requesting section 34, and stores the determination result in the RAM.

In the case where the input section 60 is a device for inputting fingerprint information, for example, fingerprint information of a registered user of the biometric information measurement device 100 which is stored in advance in the storage medium 40, and the fingerprint information which is input through the input section 60 are compared with each other. When the degree of match between the two sets of fingerprint information is equal to or larger than a threshold, it is determined that the user attached with the biometric information measurement device 100 is the registered user.

The storage controller 33 controls a process of storing biometric information calculated by the biometric information calculating section 32 in the storage medium 40. Specifically, in the case where the determination result stored in the RAM indicates that the user is a registered user, the storage controller 33 stores information (registered ID) indicating the registered user while being associated with the biometric information calculated by the biometric information calculating section 32.

In the case where the determination result stored in the RAM indicates that the user is not a registered user, the storage controller 33 stores information (dummy ID) indicating an unregistered user who is other than a registered user, while being associated with the biometric information calculated by the biometric information calculating section 32.

The attachment and detachment determining section 36 determines whether the biometric information measurement device 100 is in an attached state where the biometric information measurement device 100 is attached to the living body or the unattached state where the biometric information measurement device 100 is detached from the living body based on the output signal of the attachment and detachment detection sensor 70.

If the output signal of the attachment and detachment detection sensor 70 indicates that a contact with the living body is detected, for example, the attachment and detachment determining section 36 determines that the device is in an attached state, whereas if the output signal of the attachment and detachment detection sensor 70 indicates that a contact with the living body is not detected, the attachment and detachment determining section 36 determines that the device is in an unattached state.

The storage medium 40 of the biometric information measurement device 100 stores identification information for identifying a registered user who is requested by the doctor to use the biometric information measurement device 100. The biometric information measurement device 100 has a user registration mode in which the identification information can be stored in the storage medium 40.

Hereinafter, the operation of the biometric information measurement device 100 when the user registration mode is set will be described.

When instructions for user registration is input by a button operation or the like, the controller 30 requests an input of the identification information, stores the identification information which is input through the input section 60 in response to the request, in the storage medium 40 while being associated with the registered ID indicating a registered user, and ends the user registration mode. According to this series of processes, a user is registered as the registered user in the biometric information measurement device 100.

Figure 5:
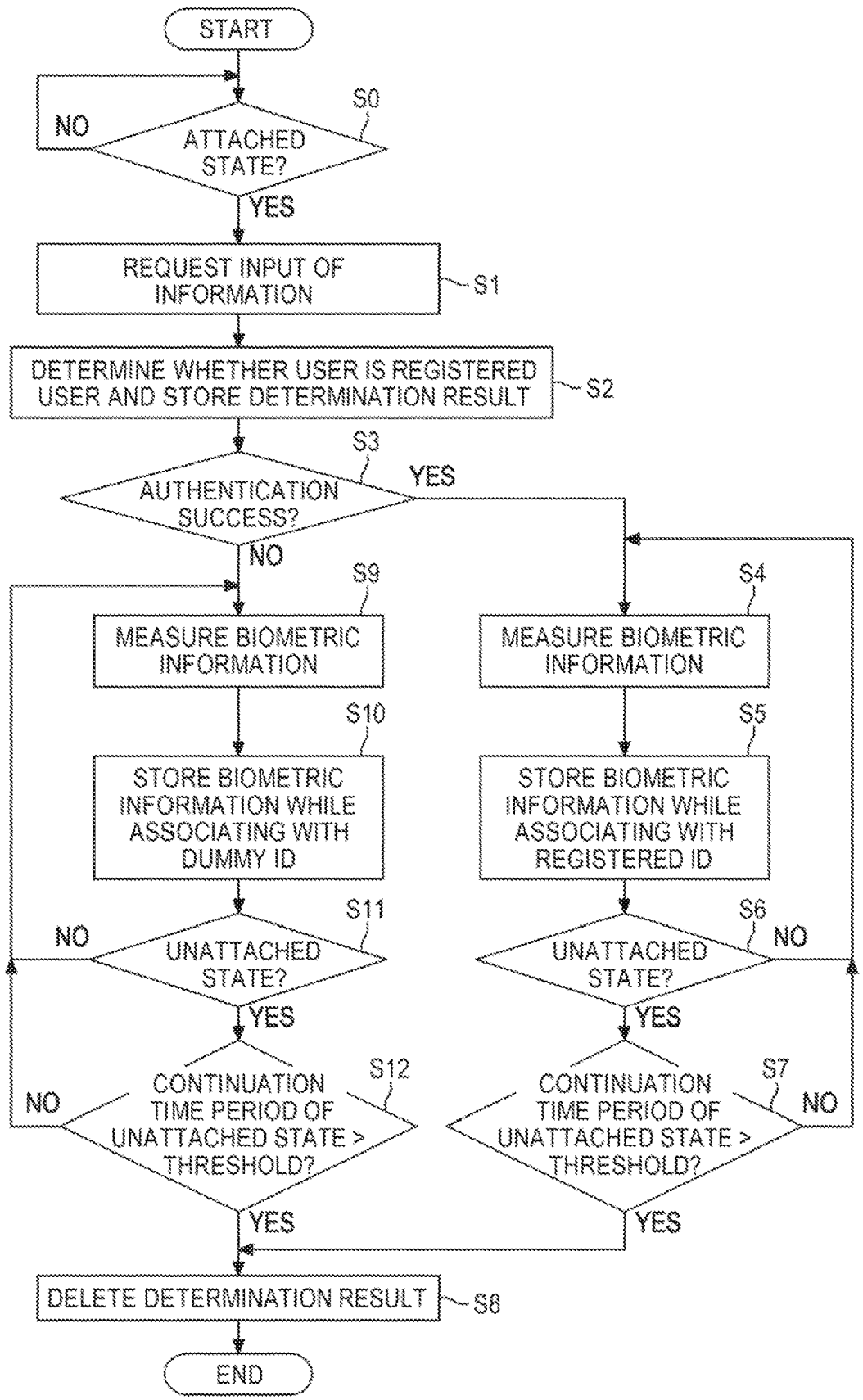
FIG. 5 is a flowchart illustrating the operation of the biometric information measurement device 100 shown in FIG. 1 in a biometric information measurement mode.

FIG. 5 is a flowchart illustrating the operation of the biometric information measurement device 100 shown in FIG. 1 in a biometric information measurement mode.

When the person to be measured attaches the biometric information measurement device 100 to the wrist and presses a power button (not shown) which is disposed in the biometric information measurement device 100, the attachment and detachment determining section 36 of the controller 30 determines whether the biometric information measurement device 100 is attached to the living body based on the output signal of the attachment and detachment detection sensor 70 (step S0). If it is determined that the device is in an attached state, the process of step S1 is performed, whereas if it is determined that the device is in an unattached state, the determination of step S0 is repeatedly performed.

In step S1, the information input requesting section 34 of the controller 30 requests an input of identification information (step S1).

For example, the information input requesting section 34 displays on the display section 50 message information for requesting an input of the identification information, such as "Fingerprint authentication is started. Place your finger on the fingerprint sensor", "Facial image authentication (iris authentication) is started. Direct your face to the camera", or "Voiceprint authentication is started. Pronounce XX to the microphone".

In combination with the display of the massage information, sound may be output from a speaker (not shown), or a vibrator (not shown) may be activated to vibrate the device, so that the user can be easily aware of the message information. Alternatively, instead of the display of the message information on the display section 50, the information input requesting section 34 may output the message information by means of voice from the speaker.

When the user inputs the identification information through the input section 60 in response to the message information thus output, the personal identifying section 35 determines whether the user attached with the biometric information measurement device 100 is the registered user based on the identification information which is input from the input section 60, and the identification information which is stored in the storage medium 40 and corresponds to the registered ID, and stores the result of the determination in the RAM (step S2).

Specifically, when the degree of match between the two sets of identification information is equal to or larger than a threshold, the personal identifying section 35 determines that the user attached with the biometric information measurement device 100 is a registered user and stores information indicating an authentication success which is a determination result, in the RAM while being associated with the date and the time.

When the degree of match between the two sets of identification information is smaller than the threshold, the personal identifying section 35 determines that the user attached with the biometric information measurement device 100 is not a registered user and stores information indicating an authentication failure which is a determination result, in the RAM while being associated with the date and the time.

In the case where the identification information is not input through the input section 60 until a lapse of a predetermined time period such as 10 seconds after the information input requesting section 34 requests an input of identification information, the personal identifying section 35 stores the information indicating an authentication failure which is a determination result, in the RAM while being associated with the date and the time.

If the determination result which is stored in the RAM in step S2 indicates an authentication success (step S3: YES), the pressing force against the wrist applied by the pressing mechanism 20 is controlled by the pressing controller 31. In this state, the biometric information calculating section 32 calculates biometric information based on the pressure pulse wave which is detected by the optimum pressure detecting element of the pressure sensor 10 (step S4).

Then, the storage controller 33 stores the biometric information calculated in step S4 in the storage medium 40 while being associated with the registered ID (step S5).

After step S5, the attachment and detachment determining section 36 of the controller 30 determines whether the device is in an attached state or an unattached state (step S6).

If it is determined that the device is an unattached state (step S6: YES), the personal identifying section 35 determines whether the time period in which the device is determined to be in an unattached state exceeds a predetermined time period (threshold). If the time period exceeds the threshold (step S7: YES), the determination result which is stored in the RAM in the process of step S2 is deleted (step S8). Then, the measurement of biometric information is stopped.

If it is determined in step S6 that the device is in an attached state (step S6: NO), and if it is determined in step S7 that the time period is equal to or smaller than the threshold (step S7: NO), the process returns to step S4, and the process of measuring biometric information and storing the measured biometric information while being associated with the registered ID is repeated.

If the determination result which is stored in the RAM in step S2 indicates an authentication failure (step S3: NO), the pressing force against the wrist applied by the pressing mechanism 20 is controlled by the pressing controller 31. In this state, the biometric information calculating section 32 calculates biometric information based on the pressure pulse wave which is detected by the optimum pressure detecting element of the pressure sensor 10 (step S9).

Then, the storage controller 33 stores the biometric information calculated in step S9 in the storage medium 40 while being associated with the dummy ID (step S10).

After step S10, the attachment and detachment determining section 36 of the controller 30 determines whether the device is in an attached state or in an unattached state (step S11).

If it is determined that the device is in an unattached state (step S11: YES), the personal identifying section 35 determines whether the time period in which the device is determined to be in an unattached state exceeds the threshold. If the time period exceeds the threshold (step S12: YES), the determination result which is stored in the RAM in the process of step S2 is deleted (step S8). Then, the measurement of biometric information is stopped.

If it is determined in step S11 that the device is in an attached state (step S11: NO), and if it is determined in step S12 that the time period is equal to or smaller than the threshold (step S12: NO), the process returns to step S9, and the process of measuring biometric information and storing the measured biometric information while being associated with the dummy ID is repeated.

According to the biometric information measurement device 100 as described above, the biometric information which is measured from a registered user, and the biometric information which is measured from an unregistered user are stored while being clearly distinguished from each other. Therefore, diagnosis of the registered user can be appropriately performed with using the measured data of the registered user.

In the biometric information measurement device 100, even if the attachment and detachment determining section 36 determines that the device is in an unattached state, when the continuation time period of the unattached state is equal to or smaller than the threshold, the measuring and storing of biometric information are intermittently performed.

Even in the case where the biometric information measurement device 100 is loosely attached to the wrist and it is determined that the device is in an unattached state for a short time period since the attachment position is displaced due to a reason such as that the user touches the biometric information measurement device 100, for example, the result of the determination performed by the personal identifying section 35 is not deleted. Therefore, re-authentication due to the erroneous determination that the device is in an unattached state does not need to be performed, so that the usability of the device can be improved.

According to the biometric information measurement device 100, when the continuation time period of the unattached state exceeds the threshold by complete detachment of the biometric information measurement device 100 from the wrist, the determination result is deleted. Therefore, an unregistered user can be prevented from measuring biometric information while impersonating a registered user.

The above-described threshold may be set to a time period (for example, about one second) which is shorter than a time period when the biometric information measurement device 100 can be replaced to the wrist of another person, so that impersonation can be prevented.

The controller 30 may display the contents of information which is stored by the storage controller 33 while being associated with biometric information, on the display section 50, so as to make notification of the contents to the user. The controller 30 functions as a notifying section. The notifying section is a functional block which is realized by executing the biometric information management program by the processor.

Specifically, if the determination in step S3 of FIG. 5 is YES, the controller 30 displays a message indicating that measurement is performed as a registered user, on the display section 50. If the determination in step S3 of FIG. 5 is NO, the controller 30 displays a message indicating that measurement is performed as a user who is not a registered user, on the display section 50.

According to this configuration, the user can know the determination result of the personal identifying section 35 through the message displayed on the display section 50. Therefore, in the case where, in spite that the user is a registered user, the user is erroneously determined as an unregistered user because of noise contamination into the input section 60, it is possible to prompt the user to take an action of re-attaching the device and performing authentication again. Since the user can take such an action, a situation where the biometric information of the registered user is stored while being associated with the dummy ID can be prevented from occurring.

The above-disclosed embodiment should be considered in all respects to be illustrative and not restrictive. The scope of the present invention is represented by the appended claims rather than the foregoing description, and all changes within the meaning and range of equivalents thereof are intended to be covered therein.

Although the biometric information measurement device 100 measures biometric information based on the pressure pulse wave which is detected by the pressure sensor 10, for example, the device may measure biometric information based on a pulse wave that is detected by a photoelectric pulse wave sensor. Alternatively, biometric information may be measured by a cuff and a pressure sensor which detects the cuff internal pressure.

Although the biometric information measurement device 100 measures biometric information every one or plural pulse, the device may measure and store biometric information at predetermined time intervals such as every 30 minute or one hour. As described above, the present invention is useful in a biometric information measurement device which intermittently measures biometric information from a living body and stores the information.

Although the biometric information measurement device 100 is used while being attached to the wrist, the device may be used while being attached to a living body portion which is other than the wrist through which the artery passes.

As described above, the following matters are disclosed in the specification.

(1) A biometric information measurement device intermittently measures biometric information from a living body in a state of being attached to the living body. The device includes: an attachment and detachment determining section which determines whether the device is in an attached state where the biometric information measurement device is attached to the living body or in an unattached state where the biometric information measurement device is detached from the living body; a personal identifying section which, in the attached state, determines whether a user attached with the biometric information measurement device is a registered user who is registered in advance and stores a result of the determination; and a storage controller which, when a determination result indicating that the user is the registered user is stored, stores information indicating the registered user while being associated with the measured biometric information. The personal identifying section deletes the determination result when a time period in which the device is determined to be in the unattached state exceeds a predetermined time period.

(2) In the biometric information measurement device according to (1), when a determination result indicating that the user is not the registered user is stored, the storage controller stores information indicating an unregistered user while being associated with the measured biometric information.

(3) The biometric information measurement device according to (2), further includes a notifying section which makes notification of contents of the information that is caused by the storage controller while being associated with the biometric information.

(4) A biometric information management method manages biometric information that is measured by a biometric information measurement device which intermittently measures biometric information from a living body in a state where the device is attached to the living body. The method includes: determining whether the device is in an attached state where the biometric information measurement device is attached to the living body or an unattached state where the biometric information measurement device is detached from the living body; in the attached state, determining whether a user attached with the biometric information measurement device is a registered user who is registered in advance and storing a result of the determination; when a determination result indicating that the user is the registered user is stored, storing information indicating the registered user while being associated with the measured biometric information; and when a time period in which the device is determined to be in the unattached state exceeds a predetermined time period, deleting the determination result.

(5) A biometric information management program is for managing biometric information that is measured by a biometric information measurement device which intermittently measures biometric information from a living body in a state where the device is attached to the living body. The program causes a computer to: determine whether the device is in an attached state where the biometric information measurement device is attached to the living body or in an unattached state where the biometric information measurement device is detached from the living body; in the attached state, determine whether a user attached with the biometric information measurement device is a registered user who is registered in advance and store a result of the determination; when a determination result indicating that the user is the registered user is stored, store information indicating the registered user while being associated with the measured biometric information; and when a time period in which the device is determined to be in the unattached state exceeds a predetermined time period, delete the determination result.

Accordingly, a biometric information measurement device, biometric information management method, and biometric information management program are provided in which biometric information that is measured from a registered user and the user can be appropriately associated with each other.

According to the present invention, a biometric information measurement device, biometric information management method, and biometric information management program is provided in which biometric information that is measured from a registered user and the user can be appropriately associated with each other.

Although the present invention has been described with reference to the specific embodiment, the present invention is not limited to the embodiment, and various changes may be made without departing from the technical concept of the disclosed invention.

The invention claimed is:
1. A biometric information measurement device, which intermittently measures biometric information from a living body in a state of being attached to the living body, the biometric information measurement device comprising:
 a personal identifying section which, in an attached state where the biometric information measurement device is attached to the living body, determines whether a user attached with the biometric information measurement device is a registered user who is registered in advance and stores a result of the determination;
 a storage controller which, when a determination result indicating that the user is the registered user is stored, associates the measured biometric information with information indicating the registered user, and stores the information indicating the registered user and stores the associated intermittently measured biometric information, and when a determination result indicating that the user is not the registered user is stored, associates the measured biometric information with information indicating an unregistered user, and stores the information indicating the unregistered user and stores the associated intermittently measured biometric information;
 an attachment and detachment sensor which includes a capacitance touch sensor or a pressure sensor which detects contact with the living body; and
 an attachment and detachment determining section which determines that the biometric information measurement device is in the attached state when an output signal of the attachment and detachment sensor indicates that the attachment and detachment sensor detects contact with the living body and determines that the biometric information measurement device is in an unattached state when an output signal of the attachment and detachment sensor indicates that the attachment and detachment sensor does not detect contact with the living body,
 wherein the personal identifying section deletes the determination result on whether the user is the registered user when a time period in which the biometric information measurement device is determined to be in the unattached state by the attachment and detachment determining section exceeds one second.

2. The biometric information measurement device according to, claim 1, further comprising:
 a notifying section which provides notification of contents of the information that is stored by the storage controller with the associated measured biometric information.

3. A method for managing biometric information that is measured by a biometric information measurement device, which intermittently measures biometric information from a living body in a state where the biometric information measurement device is attached to the living body, the method comprising:
 in an attached state where the biometric information measurement device is attached to the living body, determining whether a user attached with the biometric information measurement device is a registered user who is registered in advance and storing a result of the determination;
 when a determination result indicating that the user is the registered user is stored, associating the measured biometric information with information indicating the registered user, and storing the information indicating the registered user and storing the associated intermittently measured biometric information;
 when a determination result indicating that the user is not the registered user is stored, associating the measured biometric information with information indicating an unregistered user, and storing the information indicating the unregistered user and storing the associated intermittently measured biometric information;

determining that the biometric information measurement device is in the attached state when an output signal of an attachment and detachment sensor including a capacitance touch sensor or a pressure sensor which detects contact with the living body indicates that the attachment and detachment sensor detects contact with the living body and determining that the biometric information measurement device is in an unattached state when an output signal of the attachment and detachment sensor indicates that the attachment and detachment sensor does not detect contact with the living body; and when a time period in which the biometric information measurement device is determined to be in the unattached state exceeds one second, deleting the determination result on whether the user is the registered user.

4. A non-transitory computer readable storage storing a program for managing biometric information that is measured by a biometric information measurement device, which intermittently measures biometric information from a living body in a state where the biometric information measurement device is attached to the living body, wherein the program when executed by a computer causes the computer to:

in an attached state where the biometric information measurement device is attached to the living body, determine whether a user attached with the biometric information measurement device is a registered user who is registered in advance and store a result of the determination;

when a determination result indicating that the user is the registered user is stored, associate the measured biometric information with information indicating the registered user, and store the information indicating the registered user and store the associated intermittently measured biometric information;

when a determination result indicating that the user is not the registered user is stored, associate the measured biometric information with information indicating an unregistered user, and store the information indicating the unregistered user and store the associated intermittently measured biometric information;

determine that the biometric information measurement device is in the attached state when an output signal of an attachment and detachment sensor including a capacitance touch sensor or a pressure sensor which detects contact with the living body indicates that the attachment and detachment sensor detects contact with the living body and determine that the biometric information measurement device is in an unattached state when an output signal of the attachment and detachment sensor indicates that the attachment and detachment sensor does not detect contact with the living body; and when a time period in which the biometric information measurement device is determined to be in the unattached state exceeds one second, delete the determination result on whether the user is the registered user.

\* \* \* \* \*